United States Patent [19]

Brown

[11] 4,002,497
[45] Jan. 11, 1977

[54] THERMOELECTRIC BATTERIES

[75] Inventor: Michael Harold Brown, Didcot, England

[73] Assignee: United Kingdom Atomic Energy Authority, England

[22] Filed: Sept. 17, 1975

[21] Appl. No.: 614,178

[30] Foreign Application Priority Data

Sept. 30, 1974 United Kingdom ............ 42423/74

[52] U.S. Cl. .......................... 136/202; 128/419 P; 136/230
[51] Int. Cl.² ....................................... H01L 37/00
[58] Field of Search ............... 128/419 P; 136/202, 136/230

[56] References Cited

UNITED STATES PATENTS 3,857,738  12/1974  Brown ............................... 136/202

OTHER PUBLICATIONS

Penn et al., Nuclear Technology, vol. 13, No. 1, Apr. 1972, pp. 89 to 95.

Primary Examiner—Leland A. Sebastian
Attorney, Agent, or Firm—Larson, Taylor and Hinds

[57] ABSTRACT

A thermoelectric battery comprises a thermoelectric module in the form of a matrix of rods of alternately $p$- and $n$-type semi-conductor material connected together in the manner of a thermopile. The thermoelectric module is suspended in a casing in contact at one end with a heat sink and having attached at the other end a radio-isotope fuel capsule. The attachment of the fuel capsule is supported against shocks or rapid accelerations by a combination of spring mounting and a fibre spider.

5 Claims, 2 Drawing Figures

THERMOELECTRIC BATTERIES

This invention relates to thermoelectric batteries, for example, thermoelectric batteries for cardiac pacemakers.

The invention provides a thermoelectric battery comprising a casing enclosing an assembly comprising a heat source secured to one end of a thermoelectric unit, the other end of the thermoelectric unit being mounted in heat conducting contact with the casing, there being a space surrounding at least the heat source end of the assembly between the assembly and the casing, the heat source end of the assembly being provided with a fibre support for restraining movement of the heat source relative to the casing. This arrangement reduces stress upon the thermoelectric unit in the event that the battery is subjected to shocks or severe acceleration.

Preferably the fibre support comprises a spider formed by lengths of fibre extending between the casing and a collar on the heat source. For ease of assembly the collar is preferably a sliding fit on the heat source. In a preferred arrangement according to the invention the said other end of the thermoelectric unit is secured to a block of heat-conducting material spring biassed into contact with the casing. Conveniently the spring biassing force is transmitted through a sleeve which is a sliding fit within the casing, the sleeve abutting at one end against the said block of heat conducting material and having the fibre spider anchored to its other end.

The fibre material is chosen to provide optimum properties of strength and low thermal conductivity.

A specific construction of thermoelectric battery embodying the invention will now be described by way of example and with reference to the drawings filed herein, in which.

Figure 1:
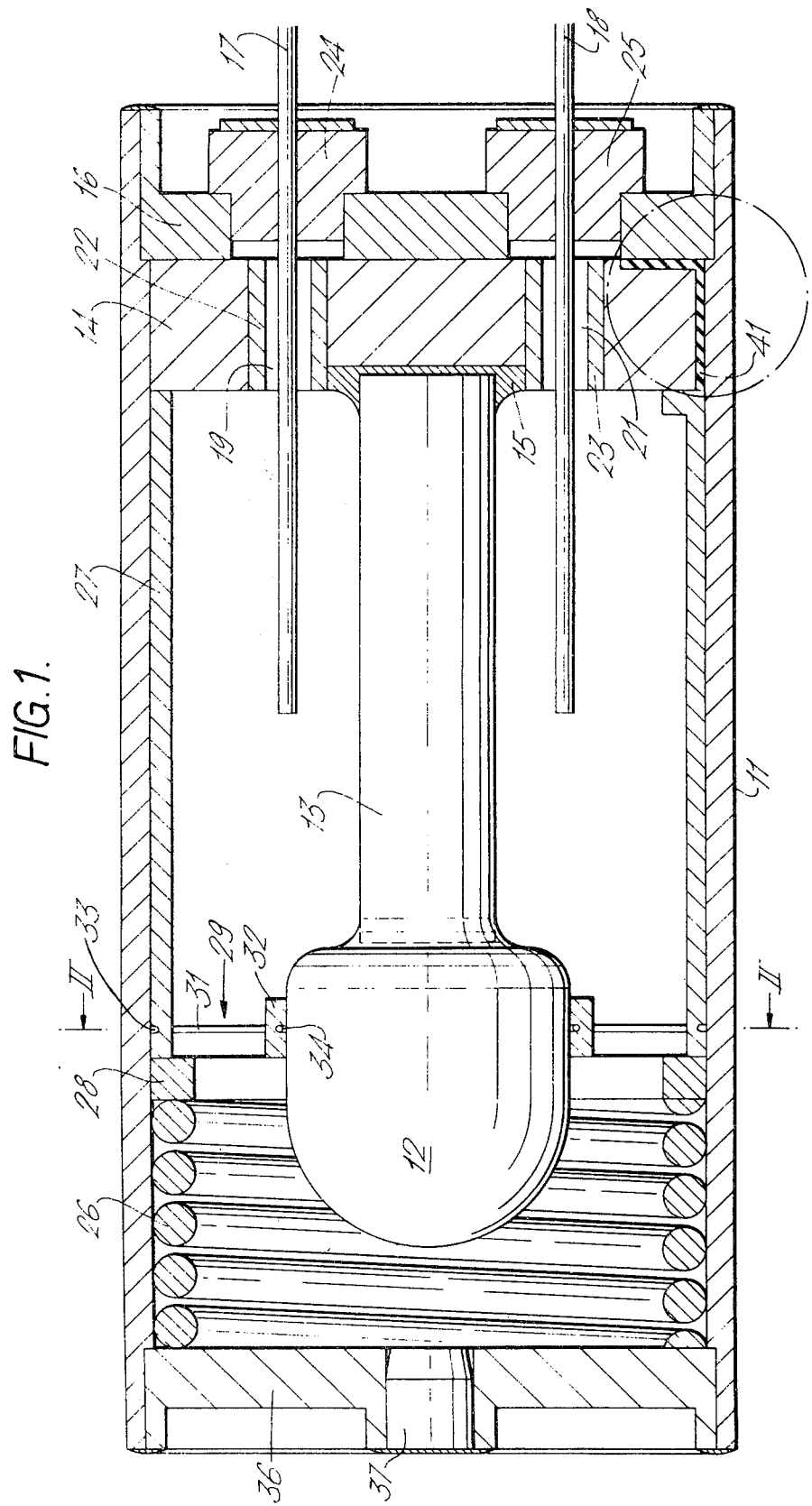
FIG. 1 is an axial section of the battery.

In this example, a cylindrical casing of stainless steel 11 encloses an assembly comprising a heat source 12 secured to one end of a thermoelectric unit which, in this example, comprises a thermoelectric module 13 in the form of a rectangular assembly of a plurality of thermoelectric elements secured together and electrically connected at their ends in the manner of a thermopile. The other end of the thermoelectric module 13 is secured with adhesive to a platform 14 of good thermal conductivity. In this example, the platform 14 is made of stainless steel and a layer 15 of epoxy resin is interposed between the thermoelectric module 13 and the platform 14 to provide electrical insulation whilst maintaining good heat conducting connection between the module and the platform.

The platform 14 abuts against an insert 16 welded into one end of the cylindrical casing 11. Electrical leads 17, 18 for making electrical connection (not shown) to the thermoelectric module 13 pass through apertures 19, 21 in the platform 14. Each of the apertures is provided with an insulating sleeve 22, 23. An electrically insulating gas-tight seal is provided at 24 and 25 between each of the electrical leads 17 and 18 respectively and the insert 16.

The platform 14 is a sliding fit within the cylindrical casing 11 and is biassed into contact with the insert 16 by the action of a spring 26 transmitted through a cylindrical sleeve 27, which is also a sliding fit within the casing 11. The sleeve 27 is of stainless steel but preferably of a different composition from that of the casing 11 to avoid possible binding. The spreader ring 28 is interposed between the spring 26 and the sleeve 27.

Figure 2:
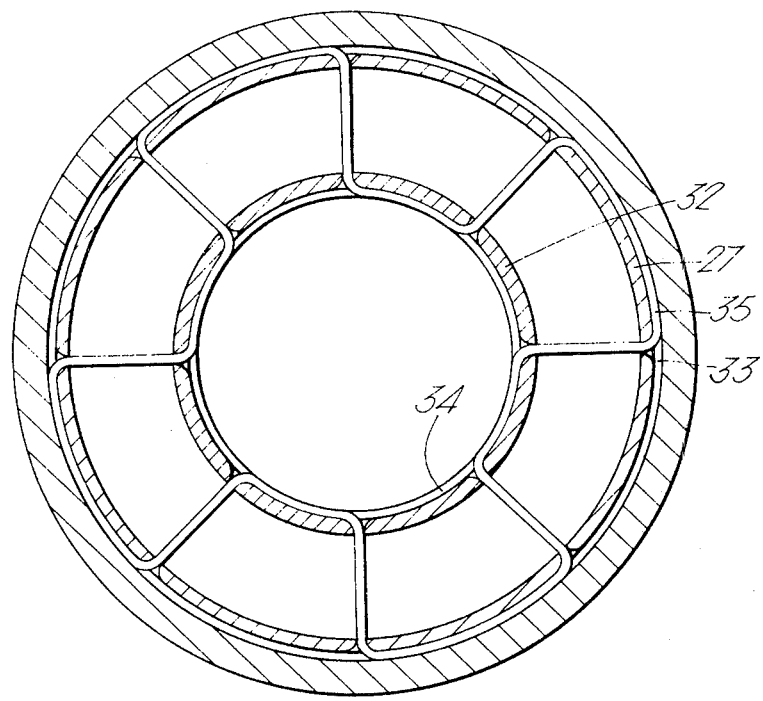
FIG. 2 is a section on the line II—II of FIG. 1 with some parts omitted.

The end of the sleeve 27 adjacent the spreader ring 28 supports a fibre spider 29. In this example, the fibre spider 29 is formed by a single fibre strand 31 which is wound in the manner best seen from FIG. 2 between the sleeve 27 and a collar 32, which is a loose sliding fit upon the heat source 12. The collar 32 and the sleeve 27 are provided with a series of radially aligned apertures connected, in the sleeve 27, by an external circumferential groove 33 and, in the collar 32, by an internal circumferential groove 34. A portion 35 of the fibre strand extends in the groove 33 around the sleeve 27 between two apertures. The strand passes through the apertures across to the corresponding apertures in the collar 32 and extends around the groove 34 in the collar 32 to emerge from the next aperture and traverse to the sleeve 27, and so on. In this way a fibre spider support is provided for the heat source 12. The portions of fibre extending in the grooves 33 and 34 are secured respectively to the sleeve 27 and the collar 32 by adhesive. The fibre material is chosen to provide optimum properties of strength and low thermal conductivity. An example of a fibre considered suitable is Du Pont's PRD 49 Type 1 described as an organic, low density, high modulus, high strength fibre resistant to abrasion, cutting and tensile failure even after looping or knotting.

The enclosure 11 is sealed by an end cap 36 welded to the enclosure 11. The end cap 36 is provided with a central pin 37 for final evacuation and gas filling after which the pin 37 is welded in place.

The thermoelectric module 13 is of the form described in British patent specification No. 1,303,834 to which reference should be made for a detailed description. Briefly, the module 13 comprises a plurality of semiconductor elements alternately of P- and N- type connected together to form a series of thermocouples by electrically conductive bridges.

The heat source 12 comprises a plutonium 238 radioisotope fuel contained in a high temperature capsule of a tungsten/tantalum alloy with an oxide surface protective layer.

It will be seen that the configuration of the components provides for easy assembly into the casing 11. The procedure is to bond the heat source 12 to the thermoelectric module 13 and the latter to the platform 14. The module leads (not shown) are then electrically connected to the leads 17 and 18 mounted in the seal housing insert 16. The assembly is inserted into the casing 11 and the insert 16 welded to the casing 11. From the other end of the casing 11, the sleeve 27 together with the fibre spider 29 are inserted, followed by spreader ring 28 and spring 26. The collar 32 slides over and locates the heat source 12 as the sleeve 27 is inserted into the casing 11. The end cap 36 is welded to the casing, the casing evacuated, filled with inert gas and the pin 37 welded to the end cap 36.

If the battery is subjected to radial shocks, the effect of these upon the heat source 12 is absorbed by the fibre spider 29, thereby reducing stress being imposed upon the thermoelectric module 13 or its bonds to the heat source 12 and the platform 14. Longitudinal shocks are cushioned by the spring 26.

The invention is not restricted to the details of the foregoing example. For instance, the interior of the sleeve 27 and the end cap 36 may be provided with radiation shielding material such as tantalum. The sleeve 27 itself may be made from tantalum and a tantalum shielding disc attached to the interior of the end cap 36 (welding difficulty making it impracticable to make the whole end cap 36 from tantalum). In such an arrangement, the spring 26 would be located at the other end of the sleeve 27, so that the sleeve more effectively "covers" the source. Provision would then be required to restrict the longitudinal movement of the assembly. Improved resistance to high frequency shocks may be achieved by providing a soft resilient material between the platform 14 and the casing 11 and end insert 16. This provision is illustrated at 41 in the circular insert of FIG. 1.

I Claim:

1. A thermoelectric battery comprising a casing enclosing an assembly comprising a heat source secured to one end of a thermoelectric unit, the other end of the thermoelectric unit being mounted in heat conducting contact with the casing, there being a space surrounding at least the heat source end of the assembly between the assembly and the casing, the heat source end of the assembly being provided with a fibre support for restraining movement of the heat source relative to the casing.

2. A thermoelectric battery as claimed in claim 1, wherein the fibre support comprises a spider formed by lengths of fibre extending between the casing and a collar on the heat source.

3. A thermoelectric battery as claimed in claim 2, wherein the collar is a sliding fit on the heat source.

4. A thermoelectric battery as claimed in claim 1, wherein the said other end of the thermoelectric unit is secured to a block of heat-conducting material spring biassed into contact with the casing.

5. A thermoelectric battery as claimed in claim 4, wherein the spring biassing force is transmitted through a sleeve which is a sliding fit within the casing, the sleeve abutting at one end against the said block of heat conducting material and having the fibre spider anchored to its other end.

* * * * *